United States Patent [19]

Seita et al.

[11] 4,205,134

[45] * May 27, 1980

[54] CARRIER FOR LIQUID CHROMATOGRAPHY

[75] Inventors: Toru Seita; Akihiko Shimizu; Yoshio Kato; Tsutomu Hashimoto, all of Shin-nanyo, Japan

[73] Assignee: Toyo Soda Manufacturing Company, Ltd., Yamaguchi, Japan

[*] Notice: The portion of the term of this patent subsequent to Dec. 19, 1995, has been disclaimed.

[21] Appl. No.: 920,988

[22] Filed: Jun. 30, 1978

Related U.S. Application Data

[62] Division of Ser. No. 849,466, Nov. 7, 1977, Pat. No. 4,128,706.

[30] Foreign Application Priority Data

Nov. 9, 1976 [JP] Japan .................................. 51-133761
Nov. 12, 1976 [JP] Japan .................................. 51-135276

[51] Int. Cl.² .................................................. C08J 9/00
[52] U.S. Cl. .................................................. 521/53
[58] Field of Search ................ 526/19, 46; 521/53

[56] References Cited

U.S. PATENT DOCUMENTS

| | | | |
|---|---|---|---|
| 3,645,996 | 2/1972 | Southland | 526/19 |
| 3,970,603 | 7/1976 | Gray | 526/19 |
| 4,038,469 | 7/1977 | Walker et al. | 526/19 |
| 4,128,706 | 12/1978 | Seita et al. | 526/19 |

*Primary Examiner*—Morton Foelak
*Attorney, Agent, or Firm*—Oblon, Fisher, Spivak, McClelland & Maier

[57] ABSTRACT

A carrier for liquid chromatography having main units $$\{CH_2-CH\}_w\{CH_2-CH\}_x\{CM\}_y\{CCM\}_z \quad (I)$$

with side groups $(CH_2)_n X'$ and $(CH_2)_m\text{-}O\text{-}(C(=O))_m\text{-}(CH_2)_q)_p\text{-}B$ wherein $n=0$ or an integer of 1 to 3; $m=0$ or 1; $q=$ an integer of 1 to 3; $p=0$ or 1; $w=90$ to 16; $x=57$ to 2; $y=0$ to 30; $z=5$ to 30; B represents adenine, guanine, thymine, uracil or cytosine; X' represents OH Cl, Br or I; and CM represents styrene, a substituted styrene, acrylonitrile, a substituted acrylonitril, acrylic acid or a substituted acrylic acid and CCM represents crosslinking agent having two or more unsaturated group such as ethylene glycol diacrylate, divinylbenzene etc.

11 Claims, 8 Drawing Figures

CARRIER FOR LIQUID CHROMATOGRAPHY

This is a division of application Ser. No. 849,466, filed Nov. 7, 1977, now U.S. Pat. No. 4,128,706.

BACKGROUND OF THE INVENTION

1. Field of the Invention

The present invention relates to a carrier for liquid chromatography for separating various compounds especially neucleic acid bases, nucleosides, nucleotides or oligonucleotides.

2. Description of the Prior Arts

The characteristics of neucleic acids are based on the mutual action between nucleic acid bases as the components of the nucleic acids. On the contrary, the neucleic acid bases, nucleosides, nucleotides and oligonucleotides as the units of the nucleic acids could be separated by utilizing the degree of the mutual action.

In fact, various resins having nucleic acid bases have been prepared from the viewpoints as follows.

(a) The polymers of N-vinyl or N-methacryloyl oxyethyl derivatives of nucleic acid bases were used. (Makromol Chem. 134, 305 (1970)).

(b) The Amberlite type resins having adenosine or guanosine component were used. (Biochem. Biophys. Acta. 80, 669 (1964)).

(c) The cellulose having guanine component was used. (Europ. Polymer J., 3 187 (1967)).

(d) The styrene-glycidyl methacrylate copolymers having nucleic acid bases were used. (Nikka 23 Aniversary N-02432 (1970) Tokyo).

These resins can not be used as the carriers for the liquid chromatography because there are certain troubles on the packing of the column and the separation factor was too low.

It is usual to use an ion-exchange resin as the carrier in the separation of nucleic acid bases by the liquid chromatography. However, in this method, various operations are needed to be complicated.

There is no report on the carrier for the liquid chromatography having high separation factor under utilizing the degree of mutual action between nucleic acid bases.

It has been known to introduce the nucleic acid base in the polymers having chloromethylstyrene component with NaH. The polymers are in the form of powder whereby the polymers cannot be used as the carriers for the liquid chromatography because of low separation factor.

SUMMARY OF THE INVENTION

It is an object of the present invention to provide a carrier for the liquid chromatography which has high separation factor.

It is another object of the present invention to provide a carrier for the liquid chromatography for separating nucleic acid bases, nucleosides, nucleotides and oligonucleotides in high separation factor.

It is the other object of the present invention to provide a carrier for the liquid chromatography prepared by bonding a nucleic acid base component in a porous gel.

The foregoing and other objects of the present invention have been attained by providing a carrier for liquid chromatography having main units;

$$\text{-}(CH_2\text{-}CH)_w\text{-}(CH_2\text{-}CH)_x\text{-}(CM)_y\text{-}(CCM)_z\text{-} \quad (I)$$

with pendant groups $(CH_2)_n X'$ and $(CH_2)_m\text{-}O\text{-}(C)_m\text{-}(CH_2)_p\text{-}B$ where the carbonyl is $\overset{\|}{O}$ wherein n=0 or an integer of 1 to 3; m=0 or 1; q=an integer of 1 to 3; p=0 or 1; w=90 to 16 and preferably 82 to 42; x=57 to 2 and preferably 30 to 8; y=0 to 30 and preferably 0; z=5 to 30 and preferably 10 to 28; B represents adenine, guanine, thymine, uracil or cytosin; X' represents OH, Cl, Br or I; CM represents styrene, a substituted styrene, acrylonitrile, a substituted acrylonitrile, acrylic acid or a substituted acrylic acid; CCM represents crosslinking agent having two or more unsaturated group such as ethyleneglycol diacrylate, divinylbenzene etc. The units of CM include styrene, substituted styrene such as alkyl styrene e.g. methyl styrene; acrylonitrile, substituted acrylonitrile such as methylacrylonitrile; acrylic acid, a substituted acrylic acid such as methacrylic acid or esters thereof.

DETAILED DESCRIPTION OF THE PREFERRED EMBODIMENTS

Figure 1:
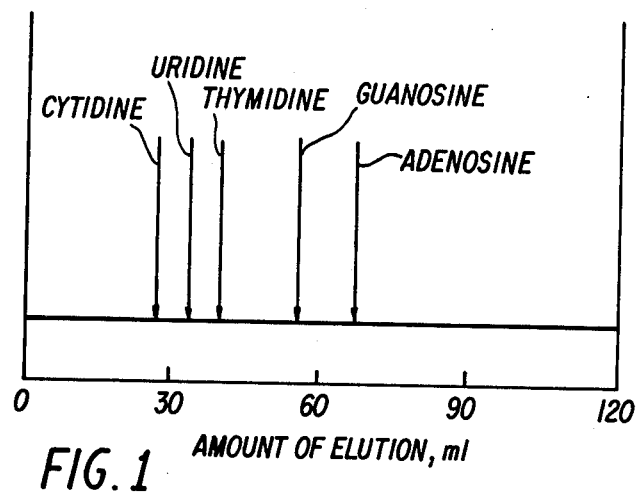

The carrier for liquid chromatography is produced by bonding a nucleic acid base component in a porous gel by reacting a nucleic acid base derivative with a porous gel having main units $$\text{-}(CH_2\text{-}CH)_{w+x}\text{-}(CM)_y\text{-}(CCM)_z\text{-} \quad (II)$$

with pendant $(CH_2)_n X'$

When X' is OH, the nucleic acid base derivative having the formula $$\underset{(CH_2)_m COCl}{\overset{B}{|}} \quad (III)$$

wherein B represents adenine, guanine, thymine, uracil or cytosine and adenine and guanine are bonded at 9-position and thymine, uracil and cytosine are bonded at 1-position, m represents an integer of 1 to 3, is used.

When X' is Cl, Br or I, the nucleic acid base derivative having the formula $$B\text{-}Y \quad (IV)$$

wherein Y represents Na or $\text{-}(CH_2)_q Z$ and Z represents OH or COOH and q represents an integer of 1 to 3 is used.

It is preferable to use the gel having main units $$\text{-}CH_2\text{-}CH\text{-} \quad (II')$$

with pendant $(CH_2)_n OH$

-continued

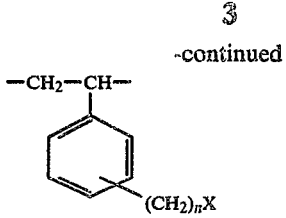
(II'')

wherein n represents 0 or an integer of 1 to 3 and X represents Cl, Br or I.

When the porous gel having the units (II') is used, it reacts with the nucleic acid base derivative having the formula

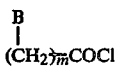
(III)

When the porous gel having the units (II'') is used, it reacts with the nucleic acid base derivative having the formula

B—Y   (IV)

In the present invention, the carrier for the liquid chromatography having excellent mechanical strength and excellent separation factor especially for separating nucleic acid bases, nucleosides nucleotides or oligonucleotides can be obtained by reacting the porous gel having the unit (II') with the nucleic acid base derivative having —COCl group or reacting the porous gel having the unit (II'') with the nucleic acid base having Na, OH or COOH group.

The carriers obtained from the crosslinked porous gel are superior to those obtained from the noncrosslinked porous gel as the carrier for the liquid chromatography from the viewpoints of shrinkage of volume and mechanical strength.

The carriers are obtained from the porous gel. Accordingly, the separation factor of the carriers is remarkably superior to those of the carriers prepared by using a powdery carrier when the carriers are used for the liquid chromatography.

Suitable base polymers for the porous gel having the units (II') include homopolymers and copolymers of a styrene derivative monomer having OH group such as hydroxystyrene, hydroxymethylstyrene (o-, m-, p- or mixtures) and copolymers of the styrene derivative monomer having OH group with a comonomer such as styrene, substituted styrenes e.g. α-methylstyrene; acrylic acid, methacrylic acid or esters thereof; acrylonitrile or substituted acrylonitriles e.g. methacrylonitrile. These polymers are crosslinked with a crosslinking agent having two or more unsaturated groups such as divinylbenzene, ethyleneglycol diacrylate etc. The porous gels prepared by graft-polymerizing the monomer for the unit (II') on a silica gel, alumina etc. can be also used as the porous gel.

It is also possible to use the monomer having the group which can be converted to the unit (II'). The resulting porous gel is hydrolyzed to convert to the unit (II').

The carriers of the present invention are prepared by reacting the nucleic acid base derivative having the formula (III) with the porous gel having the units (II') so as to bond the nucleic acid base component.

One example of the preparation of the carrier will be described.

The reaction of the nucleic acid base derivative having —CCCl group (formula (III)) with the porous gel having the units (II') can be carried out in a medium of pyridine, N,N'-dimethylformamide etc., in the presence or absence of a base at 15° to 80° C.

In the other embodiment of the preparation of the carriers of the present invention, the porous gel having haloalkylstyrene units is reacted with the nucleic acid base having Na, OH or COOH group.

Suitable base polymers for the porous gel having the unit (II'') include homopolymers and copolymers of a haloalkylstyrene such as m-chloromethylstyrene, p-chloromethylstyrene or a mixture, p-bromoethylstyrene and copolymers of the haloalkylstyrene monomer with a comonomer such as styrene, substituted styrenes e.g. α-methylstyrene; acrylonitrile, substituted acrylonitriles e.g. methacrylonitrile. These polymers are crosslinked with a crosslinking agent having two or more unsaturated groups such as divinylbenzene, ethyleneglycol diacrylate etc. The porous gels prepared by graft-polymerizing the monomer on a silica gel alumina etc. can be also used as the porous gel.

It is also possible to use the chloromethylated, porous gel prepared by chloromethylating a porous gel of a copolymer of styrene and a comonomer having two or more unsaturated groups such as divinylbenzene, ethyleneglycoldiacrylate etc. as the crosslinking agent, with chloromethyl ether etc.

The carriers of the present invention are prepared by reacting the nucleic acid base having Na, OH or COOH group with the porous gel having the units (II''), so as to bond the nucleic acid base component.

One example of the preparation of the carrier will be described.

The porous gel having the units (II'') is mixed with a nucleic acid base having Na, OH or COOH group and the reaction is carried out at 20° to 100° C.

The porous gel used in the preparation of the present invention has the physical properties of a pore diameter of 5 Å to 1 μm preferably 10 to 2000 Å especially 50 to 500 Å, and a crosslinked degree of 5 to 30 mole %; a size of gel of 2 to 200 μm preferably 5 to 50 μm. The nucleic acid base component is bonded at a ratio of 5 to 60 mole % to the porous gel.

The carriers obtained from the crosslinked porous gel are superior to those of non-crosslinked porous gel as described above.

The separation factor of the carriers of the present invention is remarkably high because the carriers are obtained from the porous gel as described above.

The carriers of the porous gel having nucleic acid base component have remarkably high separation factor in comparison with the non-treated gel. The carriers are the crosslinked porous gel having large surface area whereby the content of the nucleic acid base component can be easily increased.

In the carriers for the liquid chromatography, higher separation factor can be usually attained by decreasing the size of the carrier and shaping in a spherical form in comparison with other form.

Accordingly, it is preferable to use fine and spherical porous gel having nucleic acid base component when higher separation factor is desired.

When the carrier is used for the liquid chromatography, a distilled water can be used as the medium and it is preferably used for the sample which may be decomposed by a base or an acid. The ion-exchange group is not included, whereby the sample is not decomposed and the adverse effect of the salt is not caused.

When the quantative analysis of nucleic acid derivatives is carried out by the liquid chromatography, sometimes the true value could not be found in the measurement in an alkaline or acidic condition. However, water can be used as the medium when the carrier of the present invention is used. Accordingly, new applications can be considered.

Certain examples of the main units of the carrier of the present invention will be illustrated. In the examples, the unit

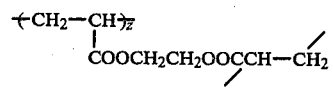

is derived from the crosslinking agent.
(w=90 to 16 preferably 82 to 42
x=57 to 2 preferably 30 to 8
y=0 to 30 preferably 0
z=5 to 30 preferably 10 to 28)

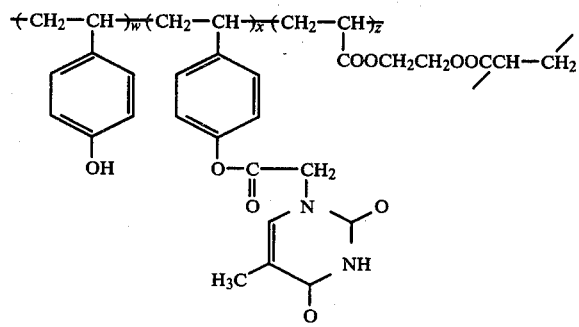

(1)

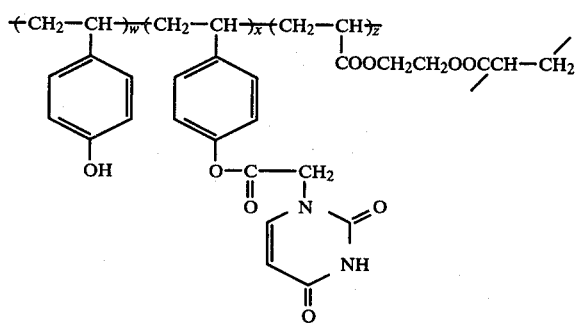

(2)

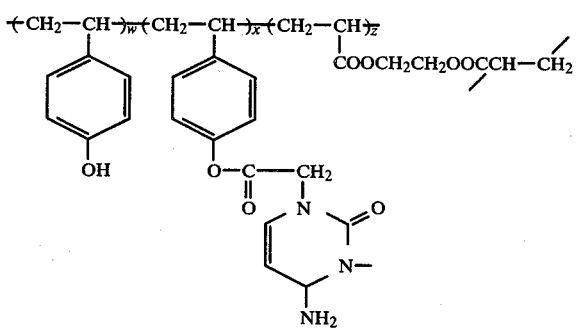

(3)

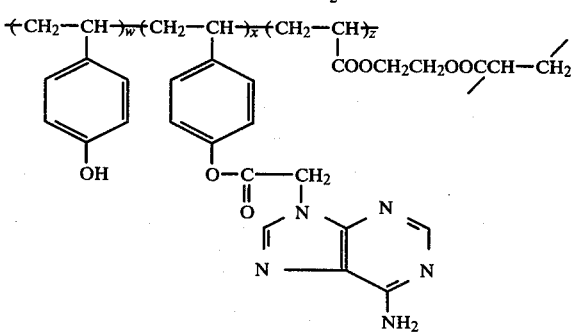

(4)

-continued
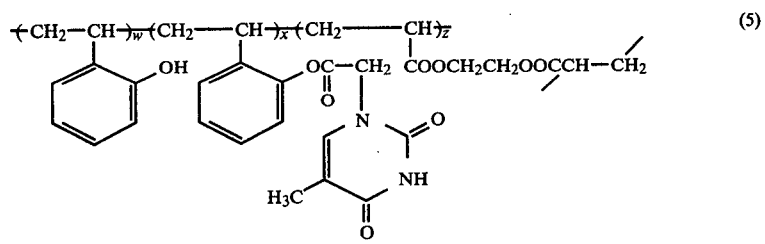 (5)
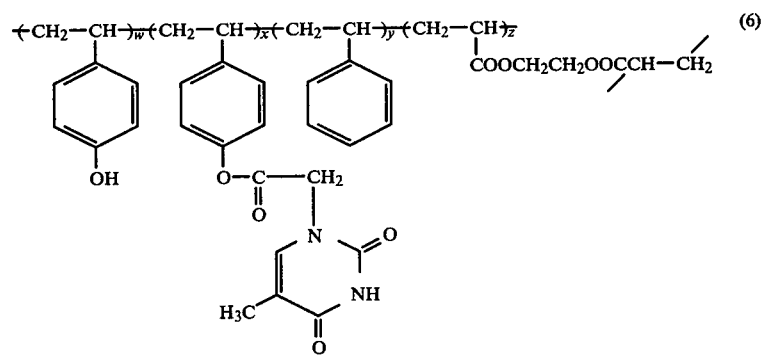 (6)
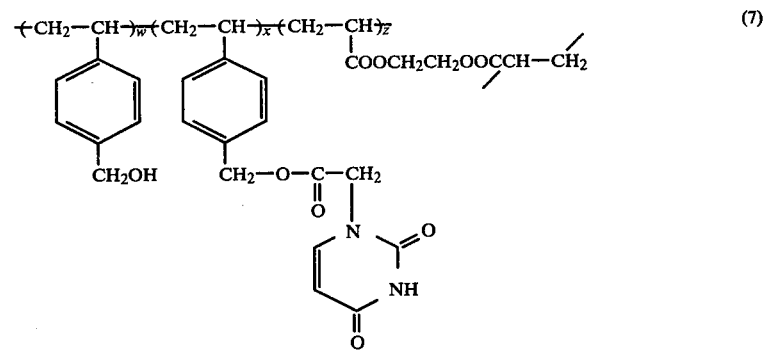 (7)
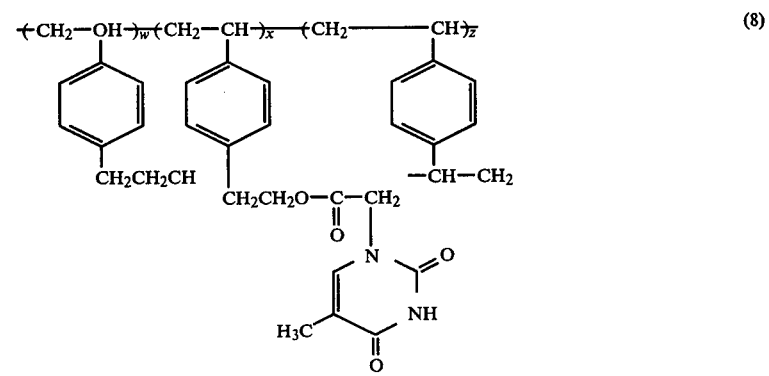 (8)
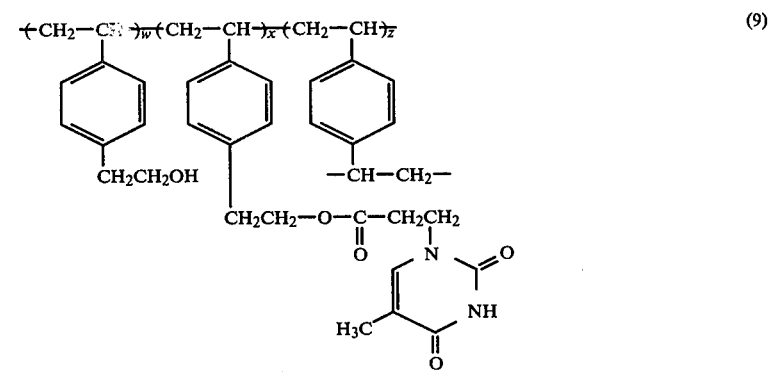 (9)

-continued
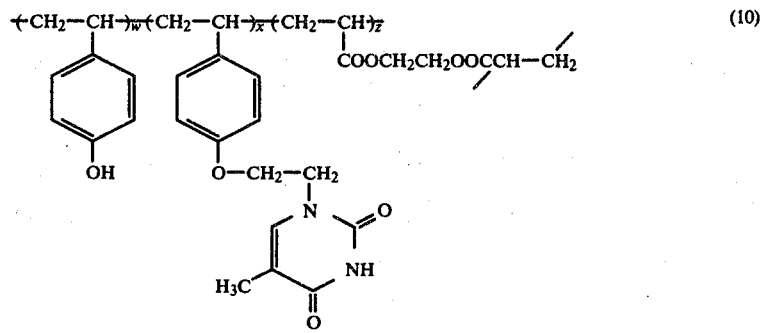 (10)
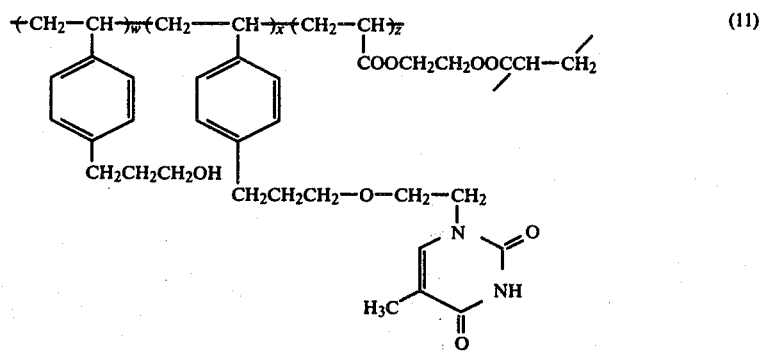 (11)
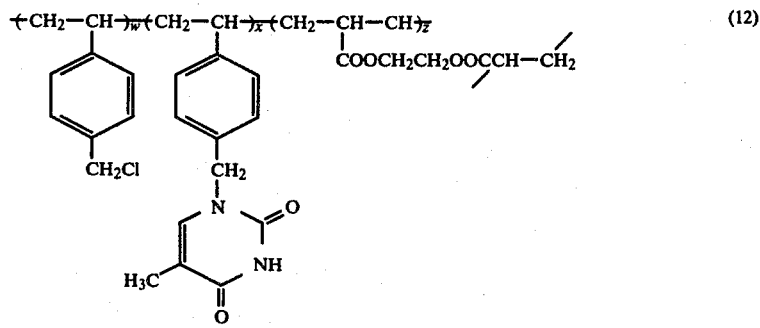 (12)
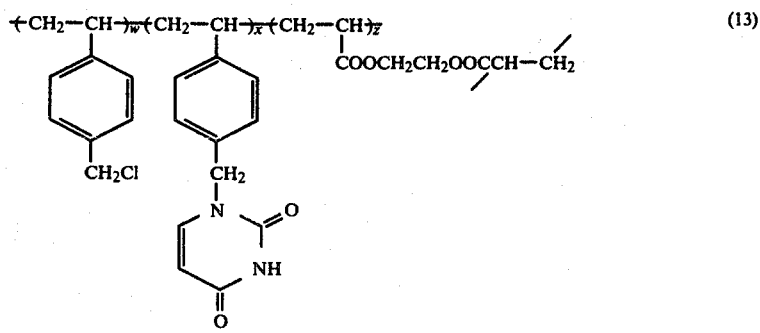 (13)
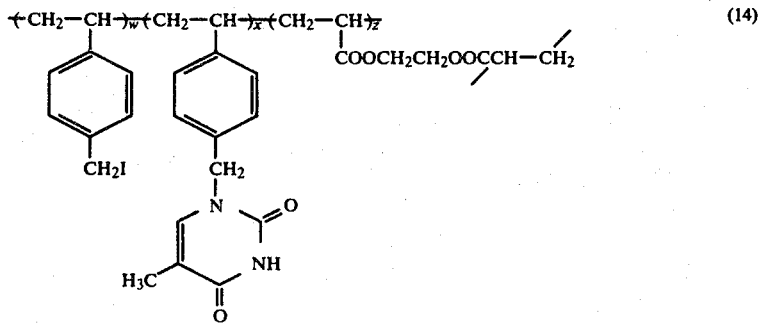 (14)

-continued
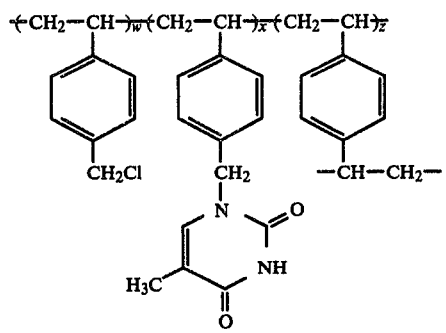 (15)
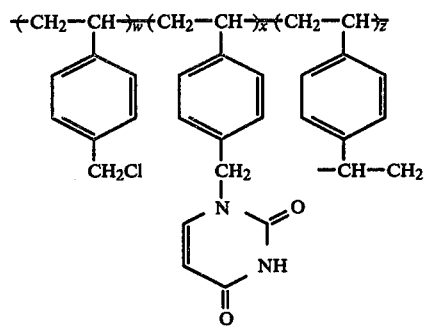 (16)
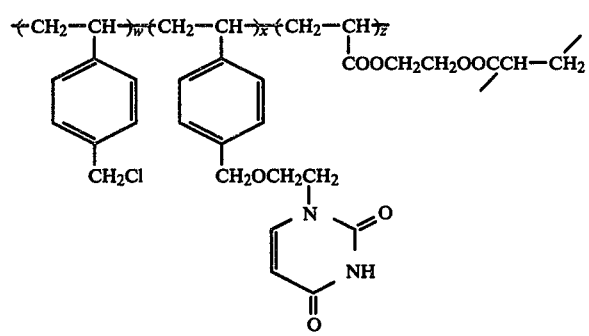 (17)
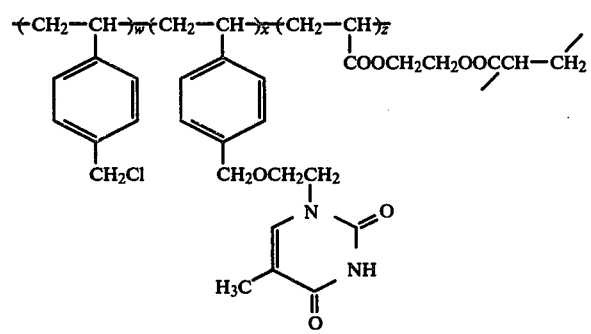 (18)
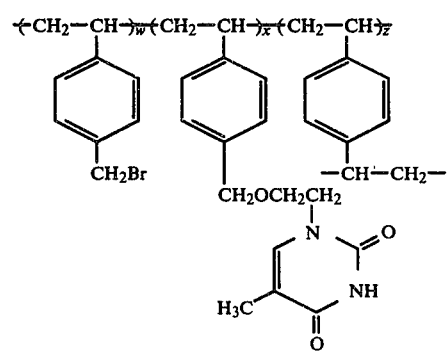 (19)

-continued
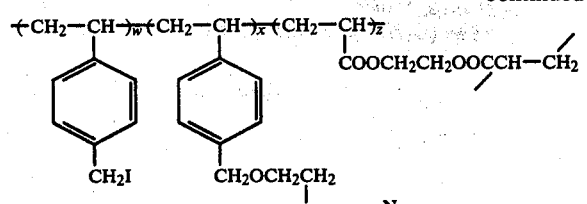  (20)
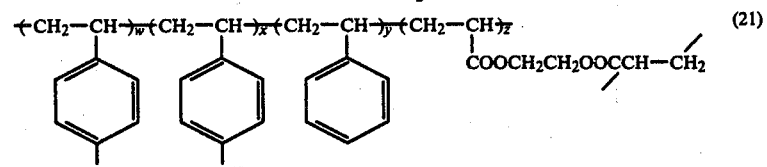  (21)
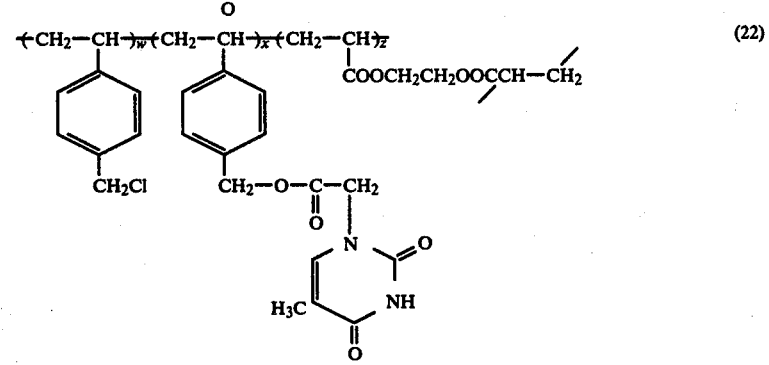  (22)
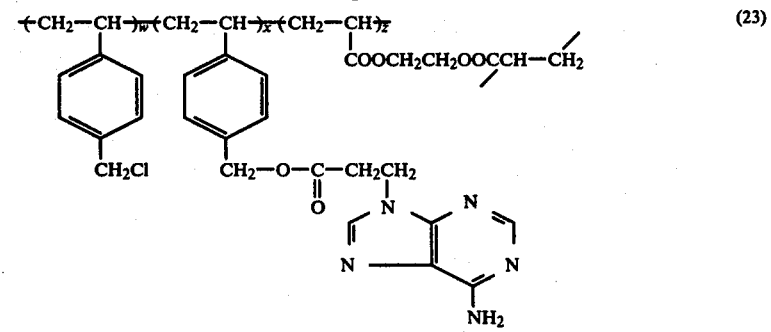  (23)
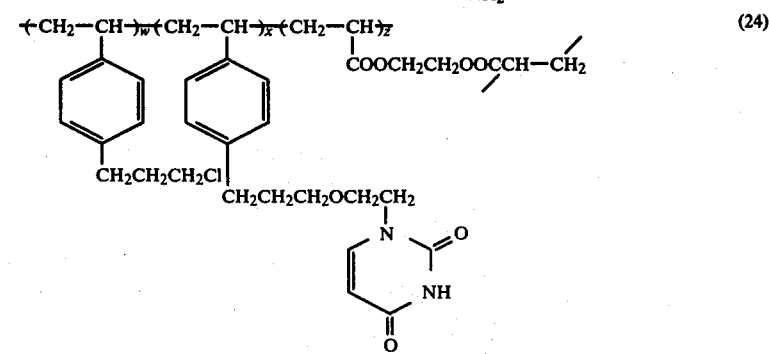  (24)

The present invention will be further illustrated by certain examples wherein the term of part means "part by weight".

EXAMPLE 1

In a reactor, 50 parts of a thymine derivative having the formula

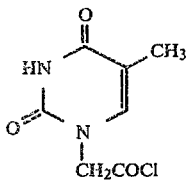

and 20 parts of a porous polyhydroxystyrene crosslinked with ethyleneglycol diacrylate (pore size of about 120 Å) and 500 parts of pyridine were charged and air in the reactor was purged by nitrogen gas and the reaction was carried out at 40° C. for 40 hours.

After the reaction, the reaction mixture was filtered and the collected impurities were removed and the reaction product was washed with ethanol and dried in vacuum.

In the infrared spectrum of the reaction product, the absorption at $1730^{cm-1}$ for ether bond and at $1670^{cm-1}$ for thymine group were found.

In the elementary analysis, the substitution of thymine was 18 mole % to OH groups in the gel.

The porous gel having thymine component was filled in a column having an inner diameter of $0.75^{cm}$ and a length of $70^{cm}$. The separation factor for nucleoside compounds was tested under the following condition. The result was shown in FIG. 1.

Figure 2:
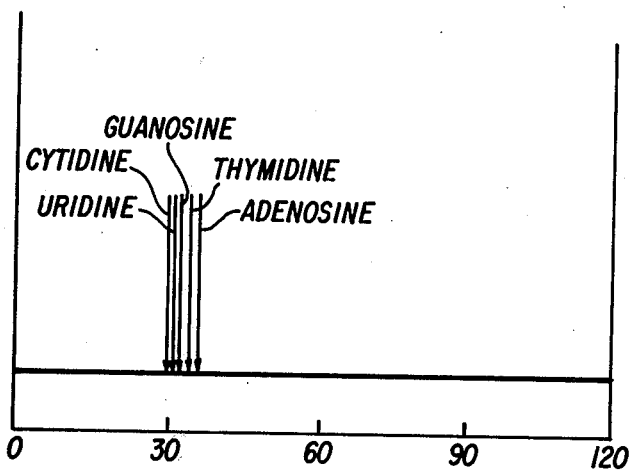

As the reference, the results in the case of using the porous gel which has no thymine component are shown in FIG. 2.

Condition of Test

Apparatus: HLC-802 UR Liquid chromatography apparatus (manufactured by Toyo Soda Co.)
Detector: Ultraviolet absorption detector (wavelength $254^{mm}$)
Medium: water
Flow speed: 3.1 ml/min.
Pressure loss: 20 Kg/cm²
Temperature: room temperature As it is clear from the results, the separation factor resulted by using the porous gel having thymine component was remarkably high. When the porous gel having no thymine component was used, the separation could not be attained.

The porous polyhydroxystyrene had main units

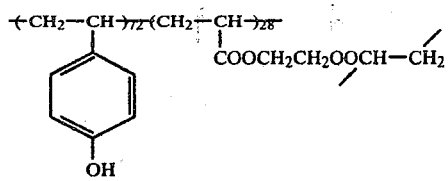

and the product had main units

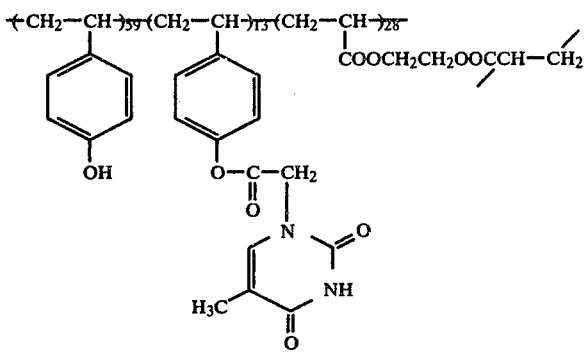

EXAMPLE 2

Figure 3:
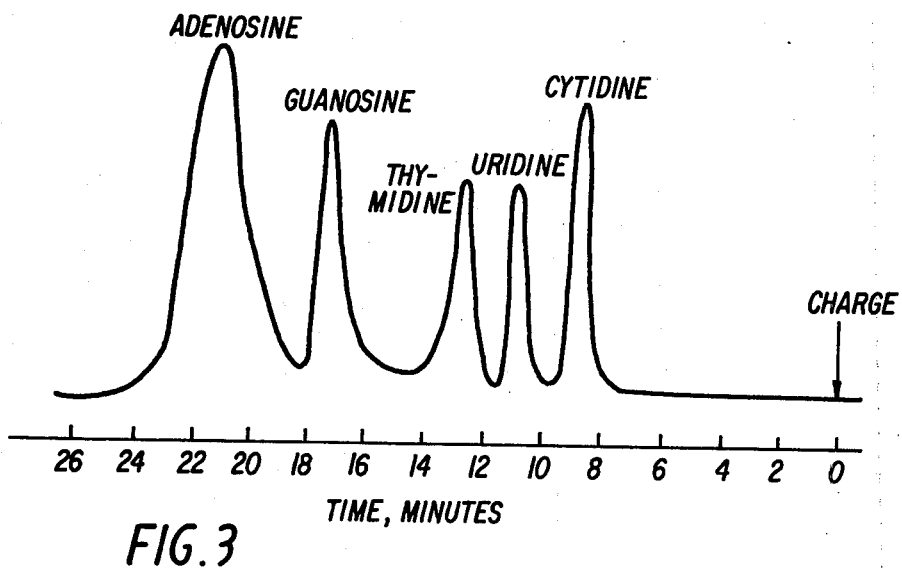

The nucleoside compounds were separated by using the gel of Example 1 under the condition of Example 1. The results are shown in FIG. 3.

EXAMPLE 3

In accordance with the process of Example 1 except reacting 50 part of the uracil derivative having the formula

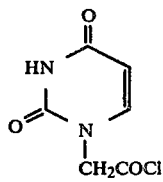

20 parts of a porous hydroxymethyl styrene crosslinked by ethyleneglycol diacrylate (pore size about 100 Å) and 500 parts of pyridine, the porous gel was obtained.

In the infrared spectrum of the reaction product, the absorptions at 1730 cm⁻¹ for ester bond and at 1650 cm⁻¹ for uracil were found.

The substitution of uracil was 15 mol % of OH group in the gel.

Figure 4:
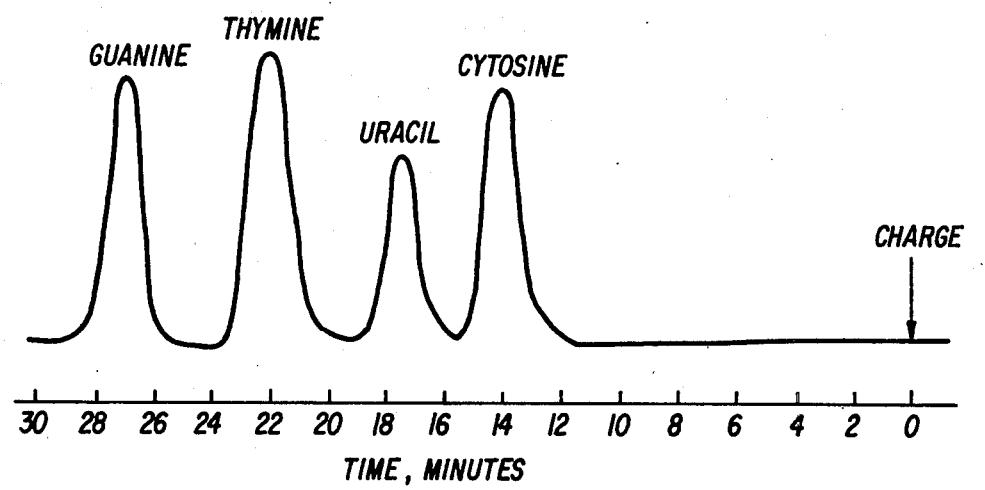

The results of the separation of the mixture of nucleic acid bases under the conditions of Example 1 using the resulting gel are shown in FIG. 4.

The porous hydroxymethyl styrene had main units $$\begin{array}{c} \text{+CH}_2\text{—CH}\text{)}_{75}\text{(CH}_2\text{—CH}\text{)}_{25}\text{—} \\ | \quad\quad\quad\quad | \\ \text{[phenyl]} \quad \text{COOCH}_2\text{CH}_2\text{OOCCH=CH}_2 \\ | \\ \text{CH}_2\text{OH} \end{array}$$

and the product had main units $$\begin{array}{c} \text{+CH}_2\text{—CH}\text{)}_{64}\text{(CH}_2\text{—CH}\text{)}_{11}\text{(CH}_2\text{—CH}\text{)}_{25}\text{—} \\ \quad\quad\quad\quad\quad\quad\quad\quad\quad | \\ \quad\quad\quad\quad\quad\quad \text{COOCH}_2\text{CH}_2\text{OOCCH=CH}_2 \\ | \quad\quad\quad | \\ \text{CH}_2\text{OH} \quad \text{CH}_2\text{—O—C—CH}_2 \\ \quad\quad\quad\quad\quad || \quad | \\ \quad\quad\quad\quad\quad \text{O} \quad \text{N} \diagup\!\!\text{O} \\ \quad\quad\quad\quad\quad\quad\quad\quad \text{NH} \\ \quad\quad\quad\quad\quad\quad\quad\quad || \\ \quad\quad\quad\quad\quad\quad\quad\quad \text{O} \end{array}$$

EXAMPLE 4

In a reactor, 50 parts of an uracil derivative having the formula $$\begin{array}{c} \text{OC}_2\text{H}_5 \\ | \\ \text{[pyrimidine ring with N, N-Na]} \\ \text{O} \end{array}$$

and 30 parts of a porous polychloromethylstyrene crosslinked ethyleneglycol diacrylate (pore size: about 100 Å) and 300 parts of N,N-dimethylformamide were charged and air in the reactor was purged by nitrogen gas and the reaction was carried out at 70° C. for 24 hours.

After the reaction, the reaction mixture was cooled to the room temperature and was filtered and the product was treated with 10% hydrochloric acid at 60° C. for 3 hours. After the treatment, the precipitate was collected and was washed with N,N-dimethylformamide and washed with ethanol and dried in vacuum.

In the elementary analysis of N, the substitution of uracil was 12 mole % to chloromethyl styrene units in the gel.

In the infrared spectrum of the reaction product, the absorption at 1673 cm$^{-1}$ for uracil group was found.

The porous gel having uracil component was filled in a column having an inner diameter of 0.75$^{cm}$ and a length of 70$^{cm}$. The separation factor for nucleoside compounds was tested under the condition of Example 1.

Figure 5:
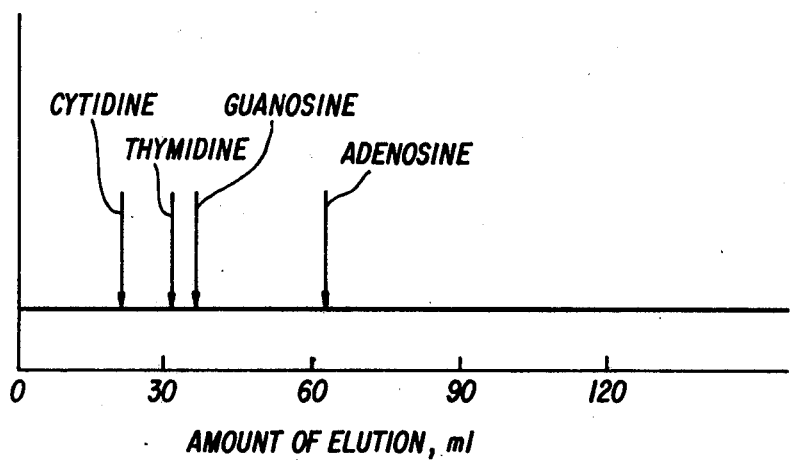

The results are shown in FIG. 5.

Figure 6:
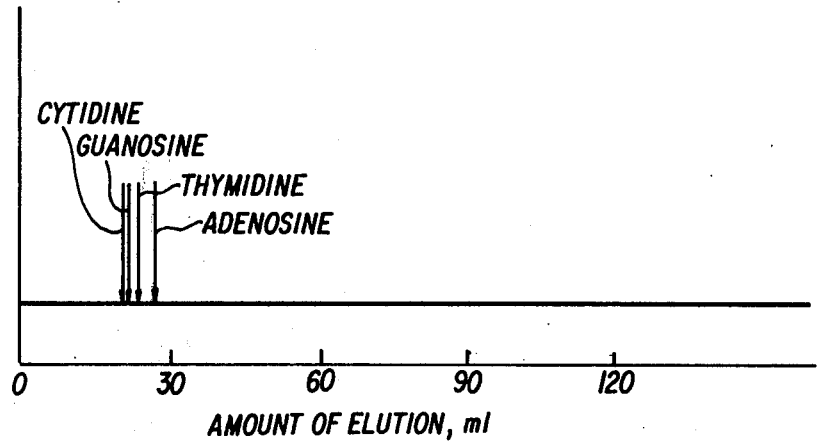

As the reference, the results in the case of using the porous gel which has no uracil component are shown in FIG. 6.

The porous polychloromethylstyrene had main units $$\begin{array}{c} \text{+CH}_2\text{—CH}\text{)}_{72}\text{(CH}_2\text{—CH}\text{)}_{28}\text{—} \\ | \quad\quad\quad\quad | \\ \text{[phenyl]} \quad \text{COOCH}_2\text{CH}_2\text{OOCCH=CH}_2 \\ | \\ \text{CH}_2\text{Cl} \end{array}$$

and the product had main units $$\begin{array}{c} \text{+CH}_2\text{—CH}\text{)}_{63}\text{(CH}_2\text{—CH}\text{)}_{9}\text{(CH}_2\text{—CH}\text{)}_{28}\text{—} \\ \quad\quad\quad\quad\quad\quad\quad\quad\quad | \\ \quad\quad\quad\quad\quad\quad \text{COOCH}_2\text{CH}_2\text{OOCCH=CH}_2 \\ | \quad\quad\quad | \\ \text{CH}_2\text{Cl} \quad \text{CH}_2 \\ \quad\quad\quad\quad | \\ \quad\quad\quad\quad \text{N} \diagup\!\!\text{O} \\ \quad\quad\quad\quad\quad\quad \text{NH} \\ \quad\quad\quad\quad\quad\quad || \\ \quad\quad\quad\quad\quad\quad \text{O} \end{array}$$

EXAMPLE 5

Figure 7:
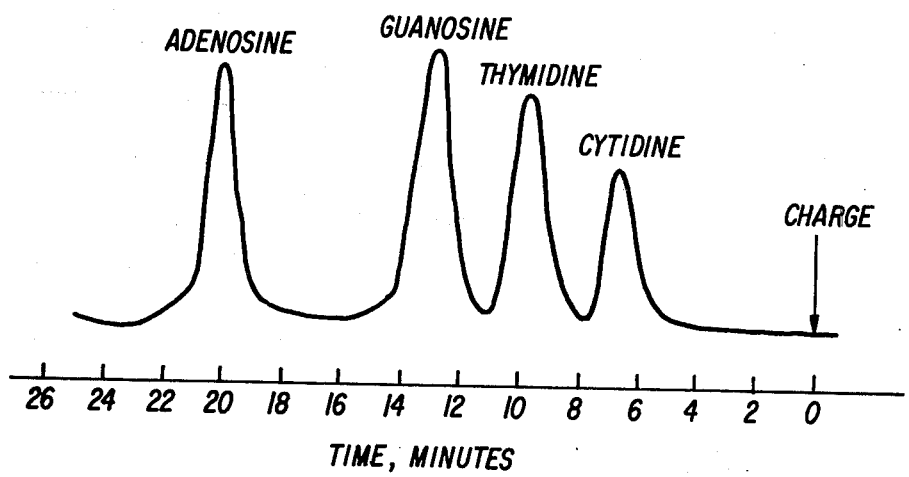

The nucleoside compounds were separated by using the gel of Example 4 under the condition of Example 1. The results are shown in FIG. 7.

EXAMPLE 6

In a reactor, purged by nitrogen gas, 50 parts of a thymine derivative having the formula

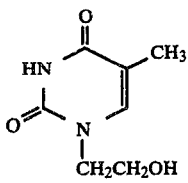

and 20 parts of oily NaH (50%) and 300 parts of N,N-dimethylformamide were charged, and the reaction of the mixture was carried out at room temperature. When the generation of nitrogen gas was stopped, 25 parts of a porous polybromomethylstyrene crosslinked (pore size: about 120 Å) was charged and the reaction was carried out at 50° C. for 10 hours.

After the reaction, the reaction product was filtered and was washed with N,N-dimethylformamide and with ethanol and was dried in vacuum.

In the elementary analysis of N, the substitution of thymine was 18 mole % to bromomethylstyrene unit in gel.

In the infrared spectrum of the reaction product, the absorption at 1676$^{cm-1}$ for thymine group was found.

The porous gel having thymine component was filled in a column having an inner diameter of 0.75$^{cm}$ and a length of 70$^{cm}$.

The separation factor for nucleoside compounds was tested under the condition of Example 1.

Figure 8:
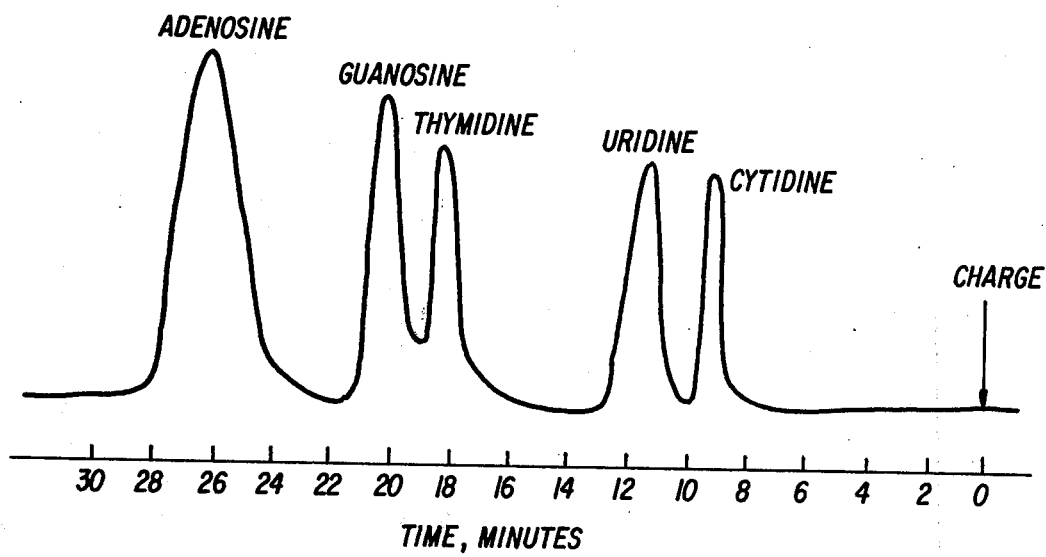

The results are shown in FIG. 8.

The porous polybromomethylstyrene had main units

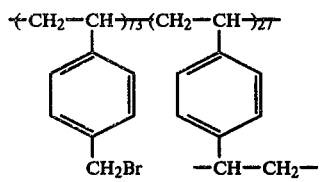

and the product had main units

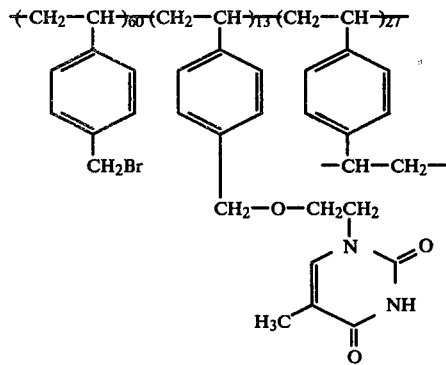

In FIG. 1, adenosine, guanosine, thymidine, uridine and cytidine are separated. In FIG. 2, adenosine, thymidine, guanosine, uridine and cytidine are separated. In FIG. 3, adenosine, guanosine, thymidine, uridine and cytidine are separated.

In FIG. 4, cytosine, uracil, thymine and guanine are separated.

In FIG. 5, adenosine, guanosine, thymidine and cytidine are separated.

In FIG. 6, adenosine, thymidine, guanosine and cytidine are separated.

In FIG. 7, cytidine, thymidine, guanosine and adenosine are separated.

In FIG. 8, cytidine, uridine, thymidine, guanosine and adenosine are separated.

What is claimed is:

1. A carrier for liquid chromatography having main units

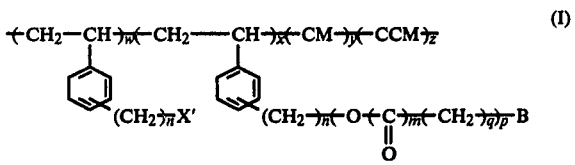

wherein n=0 or an integer of 1 to 3; m=0 or 1; q=an integer of 1 to 3; p=0 or 1; w=90 to 16; x=57 to 2, y=0 to 30 and; z=5 to 30; B represents adenine, guanine, thymine, uracil or cytosine; X' represents OH, Cl, Br or I; CM represents styrene, a substituted styrene, acrylonitrile, a substituted acrylonitrile, acrylic acid or a substituted acrylic acid and CCM represents crosslinking agent having two or more unsaturated groups, which is prepared by reacting a nucleic acid base or a derivative thereof with a porous gel having main units

2. A carrier according to claim 1 which is prepared by reacting a nucleic acid base derivative having formula

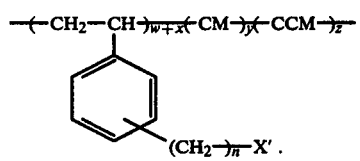

wherein n represents an integer of 1 to 3, and B represents adenine, guanine, thymine uracil or cytosine with the porous gel having units (I). with a porous gel having main units

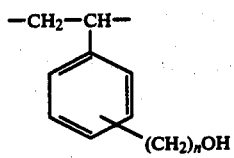
(II')

3. A carrier according to claim 1 which is prepared by reacting a nucleic acid base derivative having the formula

B—Y  (IV)

wherein Y represents Na or ―(CH$_2$)$_q$Z and Z represents OH or COOH and q represents an integer of 1 to 3; with a porous gel having main units

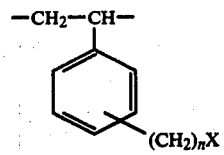
(II")

wherein n represents an integer of 1 to 3, and X represents Cl, Br or I.

4. A carrier according to claim 1 which is prepared by reacting a nucleic acid base or a derivative thereof with the porous gel in a medium.

5. A carrier according to claim 1 wherein the porous gel has a pore diameter of 10 to 2000 Å a crosslinking degree of 5 to 30 mole % and a size of gel of 2 to 200 μm.

6. A carrier according to claim 1 wherein the nucleic acid base component is bonded at a ratio of 5 to 60 mole % to the porous gel.

7. The carrier of claim 1 wherein w=82–42.

8. The carrier of claim 1 wherein x=30 to 8.

9. The carrier of claim 1 wherein y is 0.

10. The carrier of claim 1 wherein z is 10–28.

11. The carrier of claim 1 wherein said cross-linking agent CCM is selected from the group consisting of ethylene glycol diacrylate and divinylbenzene.

* * * * *